US009731089B2

(12) United States Patent
Ahmad et al.

(10) Patent No.: US 9,731,089 B2
(45) Date of Patent: Aug. 15, 2017

(54) SLEEP DETECTION FOR CONTROLLING CONTINUOUS POSITIVE AIRWAY PRESSURE THERAPY

(71) Applicant: Breathe Technologies, Inc., Irvine, CA (US)

(72) Inventors: Samir S. Ahmad, San Diego, CA (US); Leonardo Alberto Baloa Welzien, Lake Forest, CA (US)

(73) Assignee: Breathe Technologies, Inc., Irvine, CA (US)

( * ) Notice: Subject to any disclaimer, the term of this patent is extended or adjusted under 35 U.S.C. 154(b) by 475 days.

(21) Appl. No.: 14/181,431

(22) Filed: Feb. 14, 2014

(65) Prior Publication Data
US 2015/0231349 A1 Aug. 20, 2015

(51) Int. Cl.
*A61M 16/00* (2006.01)
*A61M 16/06* (2006.01)
(Continued)

(52) U.S. Cl.
CPC .... *A61M 16/0069* (2014.02); *A61M 16/0051* (2013.01); *A61M 16/06* (2013.01);
(Continued)

(58) Field of Classification Search
CPC ............ A61B 5/4806; A61M 16/0069; A61M 16/0051; A61M 2230/40; A61M 2230/42; A61M 2230/46
See application file for complete search history.

(56) References Cited

U.S. PATENT DOCUMENTS 5,458,137 A * 10/1995 Axe .......................... A61F 5/56
128/204.21
5,549,655 A * 8/1996 Erickson .............. A61N 1/3601
607/42
(Continued)

FOREIGN PATENT DOCUMENTS

WO WO 2012155251 A1 * 11/2012 ............. A61B 7/003

OTHER PUBLICATIONS

Long et al. Respiration Amplitude Analysis for REM and NREM Sleep Classification, 35th Annual International Conference of the IEEE EMBS, Jul. 3-7, 2013.*
(Continued)

*Primary Examiner* — (Jackie) Tan-Uyen T Ho
*Assistant Examiner* — Kathryn E Ditmer
(74) *Attorney, Agent, or Firm* — Stetina Brunda Garred and Brucker; Mark B. Garred

(57) ABSTRACT

A method for detecting sleep for continuous positive airway pressure (CPAP) therapy is disclosed. Discrete values of a control signal generated by a pressure controller to regulate delivered pressure at the patient are measured over a predefined time window encompassing one or more respiratory cycles. A baseline control signal value is generated from a weighted average of the measured discrete values of the control signal. Estimates of a respiratory cycle period, an inspiration control time, and an expiration control time are then generated. Estimates of one or more secondary control signal properties for each of the respective inspiration control time and expiration control time are generated. Pressure to the patient is increased in response to an evaluation of the estimates of the one or more secondary control signal properties being indicative of the patient reaching a sleep state.

12 Claims, 6 Drawing Sheets

(51) Int. Cl.
 *A61M 16/20* (2006.01)
 *A61M 16/10* (2006.01)
(52) U.S. Cl.
 CPC ......... *A61M 16/107* (2014.02); *A61M 16/208* (2013.01); *A61M 2016/0027* (2013.01); *A61M 2205/3331* (2013.01); *A61M 2205/42* (2013.01); *A61M 2205/50* (2013.01); *A61M 2205/52* (2013.01); *A61M 2230/18* (2013.01); *A61M 2230/40* (2013.01)

(56) References Cited

U.S. PATENT DOCUMENTS

| | | | | |
|---|---|---|---|---|
| 5,701,883 | A * | 12/1997 | Hete | A61M 16/12 128/204.21 |
| 5,740,795 | A * | 4/1998 | Brydon | A61M 16/00 128/204.18 |
| 7,152,598 | B2 * | 12/2006 | Morris | A61M 16/00 128/204.18 |
| 7,276,031 | B2 | 10/2007 | Norman et al. | |
| 7,938,114 | B2 | 5/2011 | Matthews et al. | |
| 2001/0004894 | A1 * | 6/2001 | Bourdon | A61M 16/0051 128/204.23 |
| 2002/0053345 | A1 * | 5/2002 | Jafari | A61M 16/00 128/204.23 |
| 2009/0078258 | A1 * | 3/2009 | Bowman | A61M 16/0051 128/204.26 |
| 2010/0319697 | A1 * | 12/2010 | Farrugia | A61M 16/10 128/204.18 |
| 2011/0197885 | A1 * | 8/2011 | Wondka | A61B 5/03 128/204.22 |
| 2012/0179061 | A1 * | 7/2012 | Ramanan | A61B 5/087 600/538 |
| 2012/0253218 | A1 | 10/2012 | Rosenthal et al. | |
| 2013/0228180 | A1 | 9/2013 | Ahmad et al. | |
| 2013/0319415 | A1 | 12/2013 | Mulcahy et al. | |

OTHER PUBLICATIONS

Cabello, Belen, and Jordi Mancebo. "Work of breathing." Applied Physiology in Intensive Care Medicine 1. Springer Berlin Heidelberg, 2012. 11-14.*
International Search Report and Written Opinion for PCT/US2015/014874. Mailed May 14, 2015.

* cited by examiner

SLEEP DETECTION FOR CONTROLLING CONTINUOUS POSITIVE AIRWAY PRESSURE THERAPY

CROSS-REFERENCE TO RELATED APPLICATIONS

Not applicable

STATEMENT RE: FEDERALLY SPONSORED RESEARCH/DEVELOPMENT

Not applicable

BACKGROUND

1. Technical Field

The present disclosure relates generally to the treatment of respiratory conditions with continuous positive airway pressure (CPAP) devices, and more particularly, to sleep detection for controlling CPAP therapy.

2. Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles resulting from patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway.

Earlier patient breathing assistance devices tended to be uncomfortable to use because of the bulkiness associated with the patient interface, as well as the misapplication of pressure resulting from sub-optimal control methodologies. Various improvements have been developed to reduce discomfort during therapy, particularly at critical points along the patient's respiratory cycle. Thus, what was previously prescribed only for the more severe cases of sleep apnea in which the benefits of treatment outweighed the significant discomfort is now useful for treating a wider spectrum of sleep apnea conditions.

Notwithstanding the increased availability of CPAP devices for home use as a result of these technical improvements, ensuring patient compliance with the prescribed treatment remains a challenge. One of the primary complaints from those patients who eventually abandon CPAP therapy is the discomfort associated with the application of pressure against respiratory efforts of the patient during a waking state. The sense of asphyxiation associated with even a slight pressure and corresponding increase in work of breathing may be distracting enough to a patient such that merely falling asleep becomes difficult.

The typical operating mode of CPAP devices requires that the patient don the ventilation interface (mask) first and then turn on the power, which in turn initiates the delivery of therapeutic pressure. If the patient has become accustomed to the pressure, then no discomfort and difficulty in falling asleep is experienced. However, some patients found that this initial pressure applied during a wakeful state is too bothersome, leading to abandonment of therapy. Earlier solutions to this issue include a ramping operating mode where the initial applied pressure is reduced to a preset level with which the patient is comfortable, and gradually increasing the pressure over a period of time until the full prescription pressure level is reached. In most cases, the duration is set to about 25 minutes.

However, there are several deficiencies and patient comfort issues that remain. Although the ramping duration is adjustable, the patient may not fall asleep during the ramp time, or conversely, the patient may fall asleep before reaching full prescription pressure and so there may be an earlier onset of obstructive events. Furthermore, following an obstructive event or other reason, the patient may prematurely awaken with the CPAP device already delivering full prescription pressure. Falling back asleep may prove difficult because of the increased pressure levels and the asphyxiation sensations resulting therefrom. Accordingly, there is a need in the art for detecting the sleeping state of a patient undergoing CPAP therapy to better control the delivery of therapeutic pressure for improved comfort.

BRIEF SUMMARY

The present disclosure contemplates improvements to CPAP therapy that controls the delivery of pressure to minimize discomfort while the patient is awake. This may involve the determination of when the patient is asleep, and only increasing pressure levels when measured respiration data is evaluated as corresponding to a sleeping state. Various embodiments contemplate a control signal evaluation, while other embodiments contemplate a work of breathing evaluation.

In accordance with one embodiment, there is a method for delivering increased pressure levels to a patient undergoing CPAP therapy in response to detection of a sleep state based on an evaluation of a control signal. The method may include measuring, over a predefined time window encompassing one or more respiratory cycles, discrete samples of the control signal as generated by a pressure controller to regulate delivered pressure at the patient. Additionally, there may be a step of generating a baseline control signal value from a weighted average of the measured discrete values of the control signal. The method may also include deriving a respiratory cycle period, an inspiration control time, and an expiration control time for each of the respiratory cycles within the predefined window. Thereafter, there may be a step of deriving peak values of the control signal for each of the inspiration control times and minimum values of the control signal for each of the expiration control times. The method may include deriving mean and standard deviation values of the peak values for each of the inspiration control times and the minimum values for each of the expiration control times. Then, the method may involve increasing pressure to the patient in response to an assessment of the patient reaching the sleep state. This may be based upon at least one of the mean and standard deviation values of the peak values for the inspiration control times and the minimum values for the expiration control times being higher than predefined threshold values.

According to another embodiment of the disclosure, a method for delivering increased pressure levels to a patient undergoing CPAP therapy in response to detection of a sleep state based on an evaluation of patient work of breathing is envisioned. The method may include measuring, over a predefined time window encompassing one or more respiratory cycles, discrete samples of a control signal generated by a pressure controller to regulate delivered pressure at the patient. There may also be a step of generating a baseline control signal value from a weighted average of the measured discrete values of the control signal. The method may also involve deriving a respiratory cycle period, an inspiration control time, and an expiration control time for each of the respiratory cycles within the predefined window. Another step may involve deriving work of breathing values from the control signal for each of the inspiration control times and expiration control times. Thereafter, the method may include deriving mean and standard deviation values of the work of breathing values for each of the inspiration control times and expiration control times. The method may proceed to increasing pressure to the patient in response to an assessment of the patient reaching the sleep state. This may be based upon at least one of the mean and standard deviation values of the work of breathing values for the inspiration control times and the expiration control times being higher than predefined threshold values.

A more broadly contemplated embodiment of the present disclosure is directed to a method for continuous positive airway pressure (CPAP) therapy. The method may include measuring, over a predefined time window encompassing one or more respiratory cycles, discrete values of a control signal generated by a pressure controller to regulate delivered pressure at the patient. There may also be a step of generating a baseline control signal value from a weighted average of the measured discrete values of the control signal. The method may also include generating estimates of a respiratory cycle period, an inspiration control time, and an expiration control time. The inspiration control time may be defined as a first duration during which the discrete values of the control signal exceed the baseline control signal. The expiration control time may be defined as a second duration during which the discrete values of the control signal are less than the baseline control signal. There may be a step of generating estimates of one or more secondary control signal properties for each of the respective inspiration control time and expiration control time. These may be over at least one of the one or more respiratory cycles within the predefined time window. Furthermore, there may be a step of increasing pressure to the patient in response to an evaluation of the estimates of the one or more secondary control signal properties indicative of the patient reaching a sleep state.

Certain other embodiments of the present disclosure contemplate a non-transitory program storage medium readable by a data processor of a CPAP therapy device that tangibly embodies one or more programs of instructions executable by the data processor to perform the foregoing methods. The present disclosure will be best understood accompanying by reference to the following detailed description when read in conjunction with the drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of certain embodiments of the presently disclosed modalities for detecting a sleeping state in a patient undergoing continuous positive airway pressure (CPAP) therapy. The application of increased pressure may be accelerated or delayed depending on whether or not the sleeping state is detected at any given time during treatment. The description sets forth the various functions in connection with the illustrated embodiments, but it is to be understood, however, that the same or equivalent functions may be accomplished by different embodiments that are also intended to be encompassed within the scope of the present disclosure. As such, the particular disclosures herein are not intended to represent the only forms that may be developed or utilized. It is further understood that the use of relational terms such as first and second and the like are used solely to distinguish one entity from another without necessarily requiring or implying any actual such relationship or order between such entities.

Figure 1:
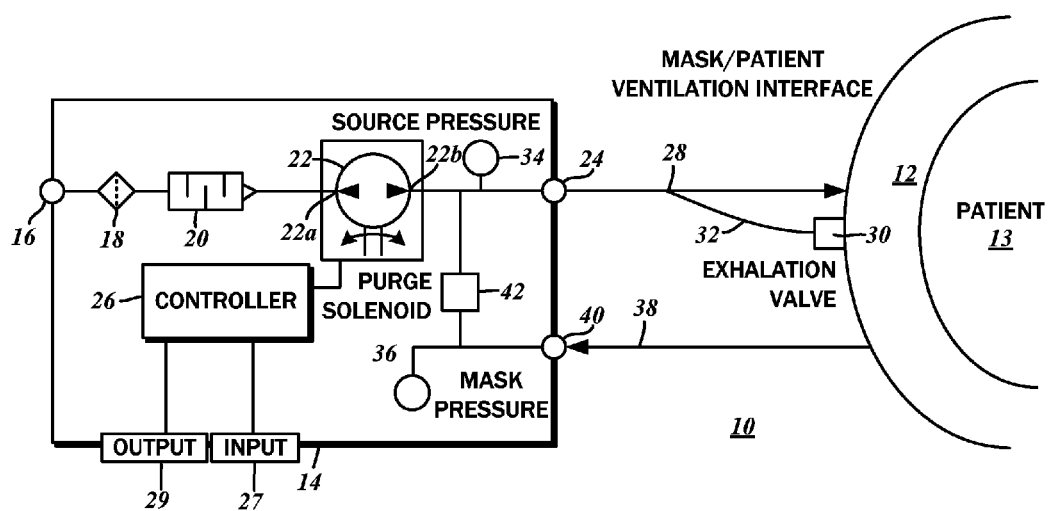
FIG. 1 is a block diagram showing the various components of a CPAP apparatus in accordance with various embodiments of the present disclosure including a typical ventilation unit, a patient ventilation mask, and gas passage conduits.

The block diagram of FIG. 1 illustrates an exemplary airway support device 10 in which various embodiments of the present disclosure may be implemented. There is a mask or patient interface 12, and a ventilation unit 14. The following disclosure will make reference to the patient interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a pressure source 22, which may be a centrifugal fan, blower, or any other suitable device that generates gas flow and pressure suitable for splinting a patient's airway with Continuous Positive Airway Pressure (CPAP) in accordance with the present disclosure. The pressure source 22 has an inlet port 22a coupled to the sound suppressor 20, and an outlet port 22b that is in gas flow communication with an outlet port 24 of the ventilation unit 14.

The pressure source 22 is driven electrically and its actuation is governed by a controller 26, which implements various methods of CPAP treatment such as those disclosed in the co-pending U.S. patent application Ser. No. 13/411,257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein. Along these lines, the controller 26 is understood to include a data processing device that receives predetermined instructions to perform various operations, and generate outputs in response. Thus, the contemplated methods for CPAP treatment that begins after the patient 13 falls asleep can be at least partially implemented therewith. There are input devices 27 that are connected to the controller 26 that accepts inputs from the patient 13, the clinician, or any other operator. The results of executing the instructions may be generated on the output devices 29.

The flow of breathing gas that is output from the pressure source 22 is passed through the outlet port 24 to a gas conduit 28 that is coupled to the aforementioned patient interface 12. The gas conduit 28 is understood to be a plastic tube having a predetermined inner diameter such as 22 mm or smaller, though any other conduit of suitable material and construction may be utilized. The patient interface 12 in accordance with various embodiments of the present disclosure also includes a piloted valve 30 that is selectively actuated depending on the pressure differential between the patient interface 12 and the ventilation unit 14. The piloted valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient interface 12, including the piloted valve 30 thereof, are presented by way of example only and not of limitation. Any other suitable patient interface 12, including those that may be utilized in conjunction with different variations of the ventilation unit 14, may be substituted without departing from the scope of the present disclosure.

In order to ascertain such pressure differentials, the presently contemplated airway support device 10 includes dual pressure sensors, including a source pressure sensor 34 and a patient interface pressure sensor 36. The source pressure sensor 34 is disposed within the ventilation unit 14, and monitors the pressure at the outlet port 22b. The patient interface pressure sensor 36 is also physically disposed within the ventilation unit 14, but is in direct gas flow communication with the patient interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

Figure 2:
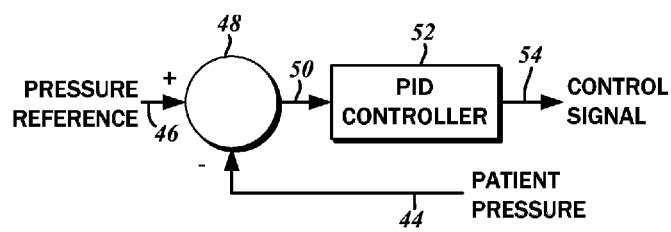
FIG. 2 is a control diagram showing an example pressure controller utilized in connection with the embodiments of the present disclosure.

With reference to the control diagram of FIG. 2, a patient interface pressure 44 is measured by the patient interface pressure sensor 36, and is compared against a reference pressure 46 at a summing point 48. In general, the reference pressure 46 is the prescribed pressure level that has been deemed necessary to splint the airway of the patient 13 to reduce instances of apnea and hypopnea. An error signal 50 resulting therefrom is provided to a proportional, integral, derivative (PID) controller 52, which is understood to be implemented on the aforementioned controller 26. The error signal 50 is the difference between the actual patient interface pressure 44 and the reference pressure 46. The PID controller 54, in turn, is understood to control the pressure source 22 to deliver the appropriate pressure level to the patient 13, as dictated by a control signal 54. In embodiments where the pressure source 22 is a blower, the control signal 54 indicates the speed or power level that is to be applied to the motor thereof in order to maintain the reference pressure 46.

Figure 3:
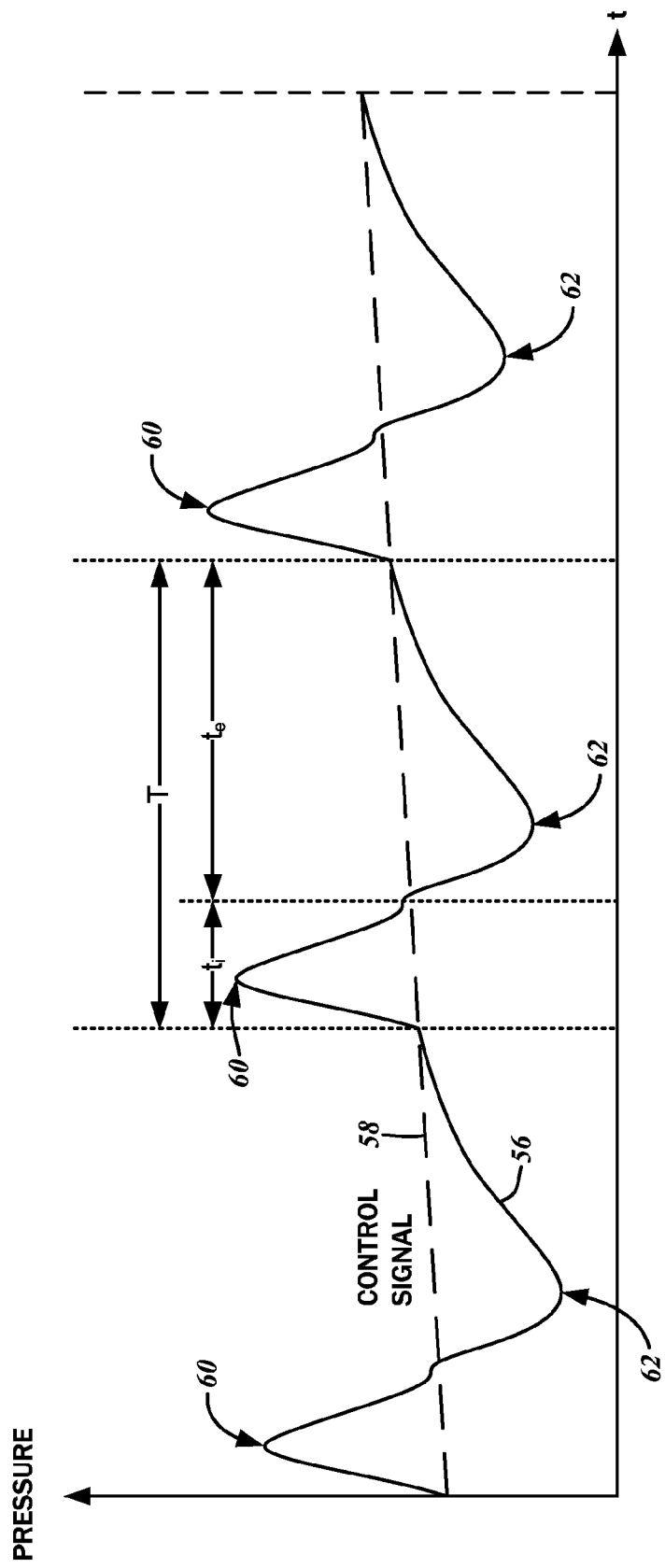
FIG. 3 is a graph illustrating exemplary respiratory cycles each defined by an inspiration control time, expiration control time, and an respiration period.

The graph of FIG. 3 shows an exemplary control signal 54 as indicated in a plot 56. Additionally shown is a plot 58 that corresponds to an average value of the control signal 54. It is understood that when the control signal 54 is greater than the average, it generally corresponds to the patient 13 being in an inspiration part of the respiratory cycle. That is, the pressure source 22 is supplying more pressure to the patient interface 12 to maintain the same reference pressure 46. When the control signal 54 is less than the average, however, this correlates to the pressure source 22 providing less pressure support and is being driven at a lower level to maintain the same reference pressure 46. This condition generally corresponds to the patient 13 being in an expiration part of the respiratory cycle. As considered herein, the varying levels of the control signal 54 is understood to be representative of various points along the respiratory cycle of the patient 13. Furthermore, the changes exhibited by the control signal 54 can also be used to determine whether or not the patient 13 has reached a sleep state in accordance with various embodiments of the present disclosure.

Figure 4:
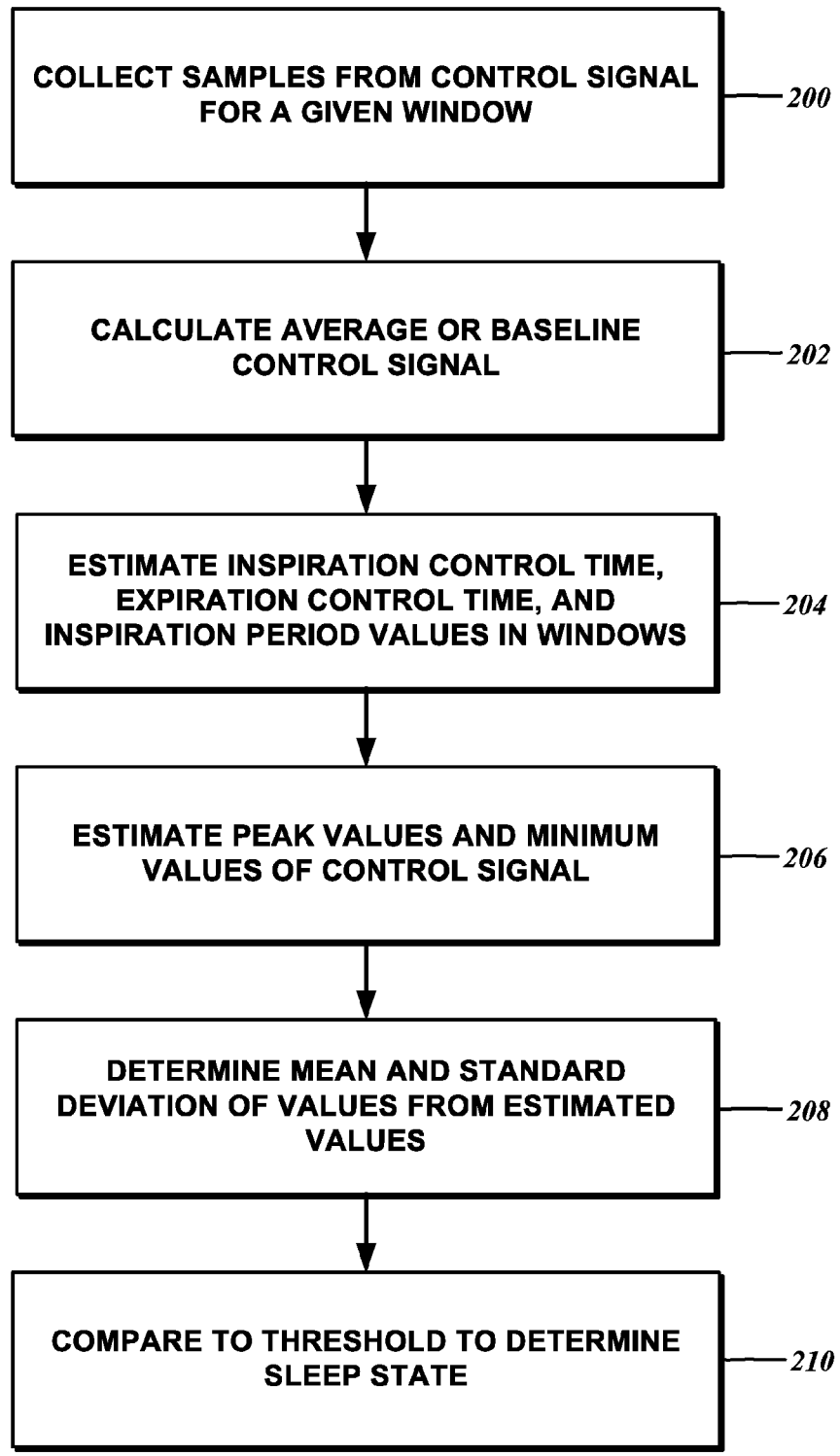
FIG. 4 is a flowchart of one embodiment of a method for delivering increased pressure levels to a patient undergoing CPAP therapy in response to detection of a sleep state based on an evaluation of a control signal.

With reference to the flowchart of FIG. 4, one embodiment of the method for delivering increased pressure levels to a patient in response to detection of the sleep state contemplates the comparison of one or more values that characterizes the control signal 54 to certain thresholds, as well as a comparison of differences between the control signal 54 at different time instants to certain thresholds. The method begins with a step 200 of measuring discrete samples of the control signal 54 as generated by the pressure controller 26/54 to regulate delivered pressure at the patient 13. The samples are understood to be from a predetermined duration window that encompasses several respiration cycles.

The method continues with a step 202 of generating a baseline control signal value from the weighted average of the aforementioned measured discrete values of the control signal 54. As best depicted in the graph of FIG. 3, this baseline control signal is shown in a plot 58. Again, when the control signal 54 is above the baseline control signal value, it is understood that the patient 13 is in the inspiration phase, but when the control signal 54 is below the baseline control signal value, the patient is in the expiration phase. The control signal 54 as corresponding to the inspiration phase and the expiration phase is characterized into its constituent parts in a step 204 of deriving estimated values of a respiratory cycle period T, an inspiration control time $t_i$, and an expiration control time $t_e$. The inspiration control time is defined as a first duration during which the discrete values of the control signal 54 exceed the baseline control signal value, and the expiration control time is defined as a second duration during which the discrete values of the control signal are less than the baseline control signal. The respiratory cycle period T is the combination of the inspiration control time $t_i$ and the expiration control time $t_e$, which represents a single breath or respiration cycle.

Next, in a step 206, peak values 60 of the control signal 54 for each of the inspiration control times in the predetermined duration window are derived, as are minimum values 62 of the control signal 54 for each expiration control times in the predetermined duration window. The peak values 60 and the minimum values 62 of the control signal 54 across the respective inspiration and expiration control times $t_i$, $t_e$ may also be referred to as secondary control signal properties in various embodiments.

In a step 208, the mean of the peak values 60 over the entirety of the predetermined duration window and the standard deviation thereof are derived. This step is also understood to include the derivation of the mean and the standard deviation of the minimum values 62 over the entirety of the predetermined duration window. Further, the means and standard deviations of the previously estimated inspiration and expiration control times $t_i$, $t_e$, and the respiratory cycle T may also be derived in accordance with the step 208. In accordance with one embodiment of the present disclosure, the mean and/or standard deviation of any one or combination of the aforementioned secondary control signal properties may be determined per the step 208, and compared against threshold values to assess whether the patient 13 has reached the sleep state in a step 210. These thresholds are understood to be defined as the lower limits of the sleep state. As an alternative to the step 208, it may be possible to compare the difference between secondary control signal properties as determined for one, current duration window and another, earlier duration window, with that difference being compared against a threshold therefor.

Figure 5:
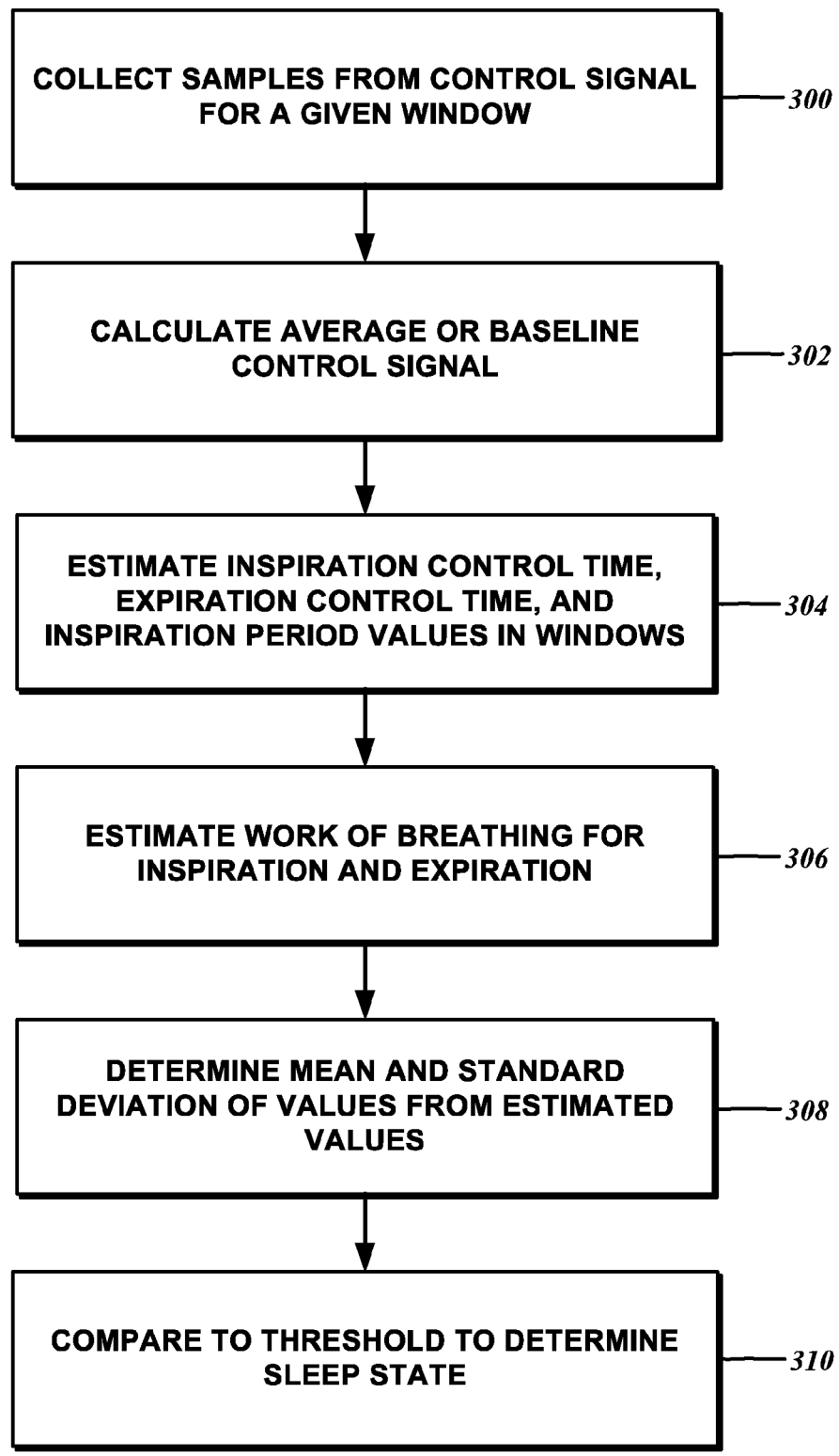
FIG. 5 is a flowchart of another embodiment of a method for delivering increased pressure levels to a patient undergoing CPAP therapy in response to detection of a sleep state based on an evaluation of patient work of breathing.

The flowchart of FIG. 5 illustrates another embodiment of the method for delivering increased pressure levels to a patient in response to detection of the sleep state. In this embodiment, the work of breathing of the airway support device 10 serves as the basis for determining whether the patient 13 is in the sleep state. Like the first embodiment of the method discussed above, the method similarly begins with a step 300 of measuring discrete samples of the control signal 54 as generated by the pressure controller 26/54 to regulate delivered pressure at the patient 13. The samples are from a predetermined duration window that encompasses several respiration cycles.

Furthermore, there is a step 302 of generating the baseline control signal value from the weighted average of the aforementioned measured discrete values of the control signal 54. The control signal 54 as corresponding to the inspiration phase and the expiration phase is characterized into its constituent parts in a step 304 of deriving estimated values of the respiratory cycle period T, the inspiration control time $t_i$, and the expiration control time $t_e$, which involves the same operations as described above.

Figure 6:
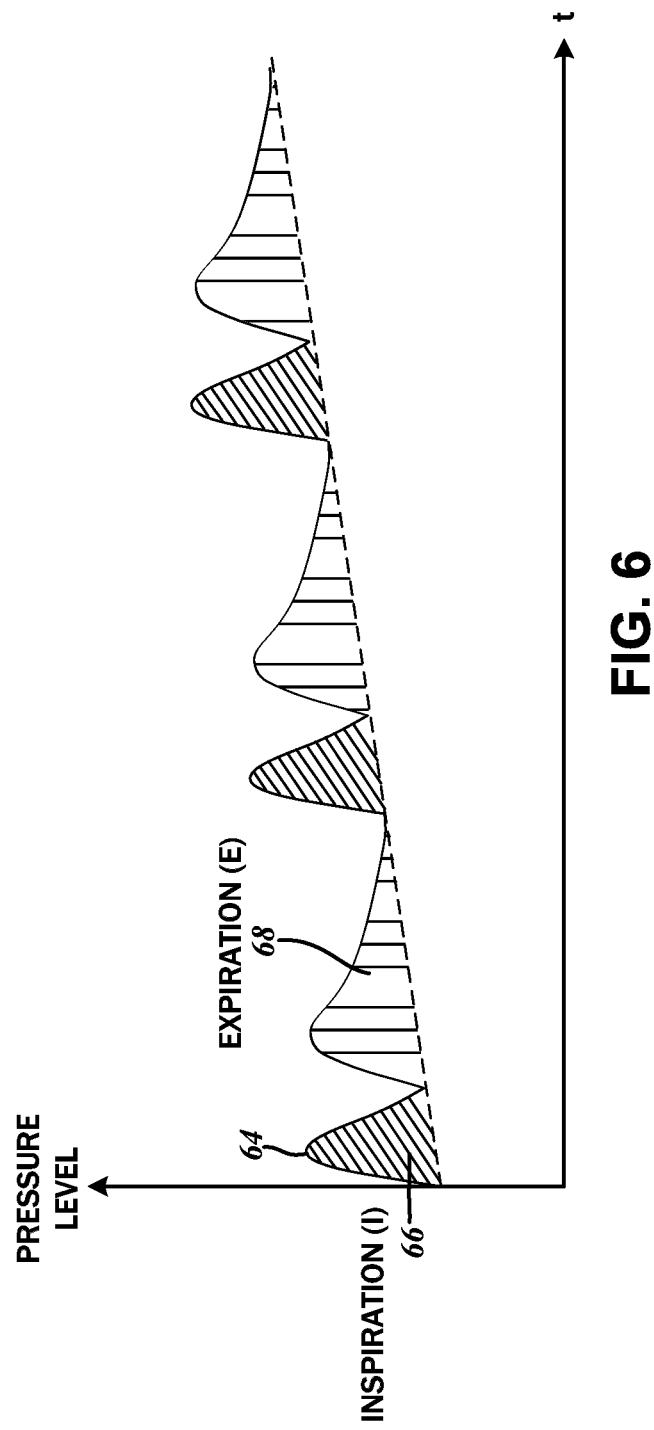
FIG. 6 is a graph illustrating exemplary respiratory cycles and work of breathing corresponding thereto.

According to a step 306, the method next involves deriving work of breathing values for the inspiration and expiration cycles of the patient respiration. As best shown in the graph of FIG. 6, which shows a plot 64 of the control signal 54, the work of breathing is defined as an area under the curve as bounded at the lower end by the minimum control signal values during the respiration cycle. Each cycle is characterized by an inspiration region 66 and an expiration region 68. The work of breathing values may likewise be generally referred to as secondary control signal properties.

The mean and standard deviation of the inspiration work of breathing values and the expiration work of breathing values over the predefined duration window are derived in accordance with a step 308. Also encompassed within this step may be deriving the means and standard deviations of the previously estimated inspiration and expiration control times $t_i$ and $t_e$, and the respiratory cycle T. The mean and/or standard deviation of any one or combination of the aforementioned secondary control signal properties may be compared against threshold values therefor that have been predetermined to correspond to the sleep state in a step 310. Instead of comparing the means and standard deviation values to threshold values, it may be possible to compare the difference between secondary control signal properties as determined for one, current duration window and another, earlier duration window, with that difference being compared against a threshold therefor. All of the various predetermined thresholds referenced herein may be partly based upon measurements made earlier in time when the patient 13 has first powered on the airway support device 10, since it may be assumed that the patient 13 was awake at such time.

Figure 7:
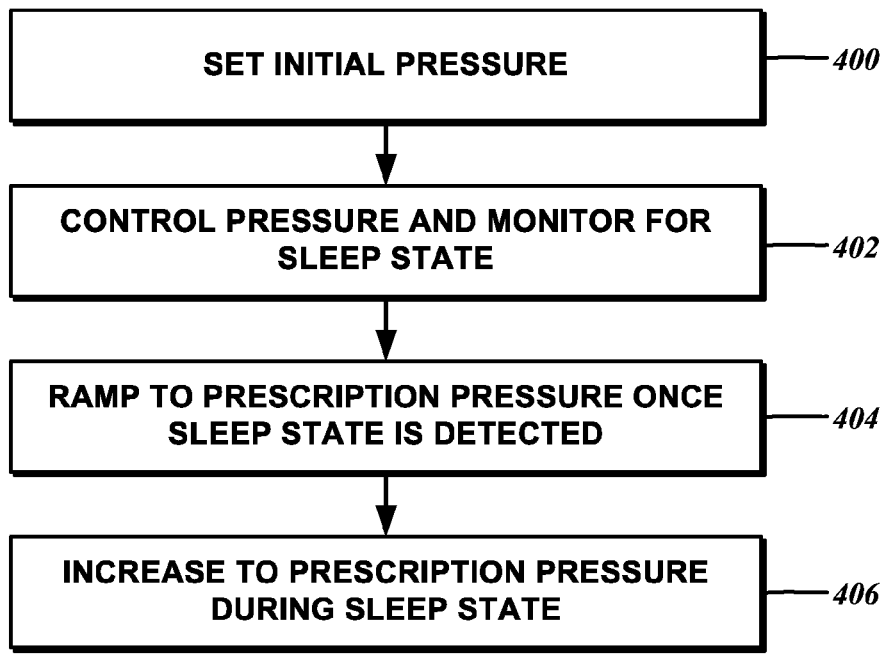
FIG. 7 is a flowchart describing a method in which the increase in pressure occurs after detecting a sleep state.

The step of increasing the pressure level delivered to the patient 13 can be variously implemented in accordance with the embodiments of the present disclosure. The flowchart of FIG. 7 depicts one such possible implementation in which the increases are applied after detecting the patient 13 in the sleep state per the steps described above. In particular, there is a step 400 of setting an initial pressure level with which the patient 13 is comfortable. This pressure level is understood to be one in which the patient 13 does not experience any sensations of suffocation, and can comfortably fall asleep while being subjected thereto. In a step 402, the set initial pressure level is delivered to the patient 13 while continuously monitoring for the onset of sleep. Upon detecting such sleep state, there is a step 404 of gradually increasing or ramping the delivered pressure to a prescription pressure level. In accordance with various embodiments, any increases of pressure level, and thus by definition the prescription pressure level, are applied exclusively during the time which the patient 13 has been evaluated to be in the sleep state. If sleep is interrupted and the patient 13 is attempting to fall asleep again, it is contemplated that the initial pressure level will resume, with any increases to the delivered pressure level being applied once the sleep state has been detected again.

Figure 8:
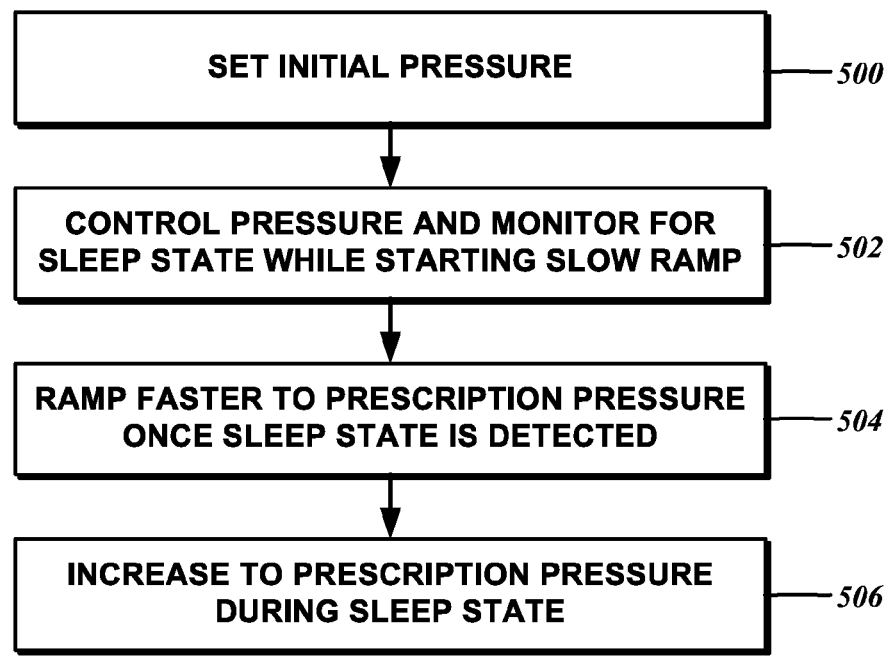
FIG. 8 is a flowchart describing a different method in which the increase in pressure includes a ramping period before detecting a sleep state.

An alternative implementation involves a gradual increase in the delivered pressure level while still in a non-sleep state as per conventional ramping modalities. This implementation is depicted in the flowchart of FIG. 8, which again, begins with a step 500 of setting an initial pressure level that the patient 13 finds to be comfortable. Next, according to a step 502, the delivered pressure level is slowly increased at a first ramping rate or slope, regardless of whether the patient 13 is falling asleep or not. Once the sleep state is detected, the ramping rate is increased at a level greater than the first ramping rate in accordance with a step 504. Increases of pressure level are applied at the second, faster rate exclusively during the time which the patient 13 has been evaluated to be in the sleep state. As with the previous implementation, the prescription pressure level is delivered when the patient 13 is asleep.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. A method for continuous positive airway pressure (CPAP) therapy comprising:
   measuring, over a predefined time window encompassing one or more respiratory cycles, discrete values of a control signal generated by a pressure controller to regulate delivered pressure at the patient;
   generating a baseline control signal value from a weighted average of the measured discrete values of the control signal;
   generating estimates of a respiratory cycle period, an inspiration control time, and an expiration control time, the inspiration control time being defined as a first duration during which the discrete values of the control signal exceed the baseline control signal, and the expiration control time being defined as a second duration during which the discrete values of the control signal are less than the baseline control signal;
   generating estimates of one or more secondary control signal properties for each of the respective inspiration control time and expiration control time over at least one of the one or more respiratory cycles within the predefined time window, the one or more secondary control signal properties including work of breathing values derived from the control signal for the inspiration control time and the expiration control time respectively, the work of breathing values being defined as the area between the control signal and the baseline control signal; and
   increasing pressure to the patient in response to an evaluation of the estimates of the work of breathing values indicative of the patient reaching a sleep state.

2. The method of claim 1, further comprising:
   deriving, over the predefined time window, mean and standard deviation values of the estimates of the work of breathing values;
   wherein the evaluation of the estimates of the work of breathing values includes a comparison of the mean and standard deviation values of at least one of the estimates of the work of breathing values to corresponding predefined threshold values thereof.

3. The method of claim 1, wherein the evaluation of the estimates of the work of breathing values includes:
   deriving a difference between a first set of the estimates of the work of breathing values from a current predefined time window and a second set of the estimates of the work of breathing values from a previous predefined time window;
   wherein the difference being higher than a predefined threshold is indicative of the patient reaching the sleep state.

4. The method of claim 1, further comprising:
   receiving an initial pressure level from a patient; and
   delivering the initial pressure level to the patient while in a non-sleep state.

5. The method of claim 4, wherein the pressure is increased to a prescription pressure level from the initial pressure level in response to the evaluation of the estimates of the work of breathing values indicating the patient reaching the sleep state.

6. The method of claim 4, further comprising:
   ramping pressure to the patient while in the non-sleep state from the initial pressure level to a prescription pressure level at a first predetermined rate;
   wherein the pressure is increased to the prescription pressure level at a second predetermined rate higher than the first predetermined rate in response to the evaluation of the estimates of the work of breathing values indicating the patient reaching the sleep state.

7. A method for delivering increased pressure levels to a patient undergoing CPAP therapy in response to detection of a sleep state based on an evaluation of patient work of breathing, the method comprising:
   measuring, over a predefined time window encompassing one or more respiratory cycles, discrete samples of a control signal generated by a pressure controller to regulate delivered pressure at the patient;
   generating a baseline control signal from a weighted average of the measured discrete samples of the control signal;
   deriving a respiratory cycle period, an inspiration control time, and an expiration control time for each of the respiratory cycles within the predefined window;
   deriving work of breathing values from the control signal for each of the inspiration control times and expiration control times, the work of breathing values being defined as the area between the control signal and the baseline control signal;
   deriving mean and standard deviation values of the work of breathing values for each of the inspiration control times and expiration control times; and
   increasing pressure to the patient in response to an assessment of the patient reaching the sleep state based upon at least one of the mean and standard deviation values of the work of breathing values for the inspiration control times and the expiration control times being higher than predefined threshold values.

8. The method of claim 7, wherein:
   the inspiration control time is defined as a first duration during which the measured discrete samples of the control signal exceed the baseline control signal; and
   the expiration control time is defined as a second duration during which the measured discrete samples of the control signal are less than the baseline control signal.

9. The method of claim 7, further comprising:
   receiving an initial pressure level from a patient; and
   delivering the initial pressure level to the patient while in a non-sleep state.

10. The method of claim 9, wherein the pressure is increased to a prescription pressure level from the initial pressure level in response to the assessment of the patient reaching the sleep state.

11. The method of claim 9, further comprising:
ramping pressure to the patient while in the non-sleep state from the initial pressure level to a prescription pressure level at a first predetermined rate;
wherein the pressure is increased to the prescription level at a second predetermined rate higher than the first predetermined rate in response to the assessment of the patient reaching the sleep state.

12. An article of manufacture comprising a non-transitory program storage medium readable by a data processor of a CPAP therapy device, the medium tangibly embodying one or more programs of instructions executable by the data processor to perform a method for continuous positive airway pressure (CPAP) therapy comprising:
measuring, over a predefined time window encompassing one or more respiratory cycles, discrete values of a control signal generated by a pressure controller to regulate delivered pressure at the patient;
generating a baseline control signal value from a weighted average of the measured discrete values of the control signal;
generating estimates of a respiratory cycle period, an inspiration control time, and an expiration control time, the inspiration control time being defined as a first duration during which the discrete values of the control signal exceed the baseline control signal, and the expiration control time being defined as a second duration during which the discrete values of the control signal are less than the baseline control signal;
generating estimates of one or more secondary control signal properties for each of the respective inspiration control time and expiration control time over at least one of the one or more respiratory cycles within the predefined time window, the one or more secondary control signal properties including work of breathing values derived from the control signal for the inspiration control time and the expiration control time respectively, the work of breathing values being defined as the area between the control signal and the baseline control signal; and
increasing pressure to the patient in response to an evaluation of the estimates of the work of breathing values indicative of the patient reaching a sleep state.

\* \* \* \* \*